United States Patent [19]

Grenier et al.

[11] Patent Number: 5,635,406
[45] Date of Patent: Jun. 3, 1997

[54] STABILIZED STANDARDS AND CALIBRATORS CONTAINING RAPAMYCIN AND TACROLIMUS BOUND TO ANTI-RAPAMYCIN AND ANTI-TACROLIMUS ANTIBODIES

[75] Inventors: Frank Grenier; Thomas F. Holzman, both of Libertyville; Allan H. Smith, Zion; Alan C. Tsurutani, Chicago, all of Ill.

[73] Assignee: Abbott Laboratories, Abbott Park, Ill.

[21] Appl. No.: 474,589

[22] Filed: Jun. 7, 1995

[51] Int. Cl.[6] .................... G01N 33/536; C07K 16/14
[52] U.S. Cl. .................. 436/536; 436/8; 435/7.1; 530/388.5
[58] Field of Search ................ 436/536, 8, 15; 435/7.1; 530/350, 387.1, 388.5

[56] References Cited

FOREIGN PATENT DOCUMENTS

| 0293892 | 7/1988 | European Pat. Off. . |
| 9218527 | 10/1992 | WIPO . |
| 9424304 | 10/1994 | WIPO . |
| 9500174 | 1/1995 | WIPO . |

*Primary Examiner*—Paula K. Hutzell
*Assistant Examiner*—Nancy A. Johnson
*Attorney, Agent, or Firm*—John F. Levis

[57] ABSTRACT

The present invention is directed to an in vitro aqueous composition comprising a drug, preferably tacrolimus or rapamycin, having enhanced stability. The invention utilizes a binding protein, preferably antibodies to tacrolimus or rapamycin, to stabilize the drug in an aqueous matrix.

42 Claims, 12 Drawing Sheets

FIG. 1

| DAY OF ASSAY / TEMPERATURE | | pH 6.1 —FKBP | pH 6.1 +FKBP | pH 7.4 —FKBP | pH 7.4 +FKBP |
|---|---|---|---|---|---|
| 0 | | 19.0 | 19.0 | 19.4 | 18.0 |
| 3 | 2–8 °C | n.d. | n.d. | 19.3 | 19.3 |
|   | 37 °C | n.d. | n.d. | 6.6 | 19.0 |
|   | 45 °C | n.d. | n.d. | 3.6 | 21.3 |
| 6 | 2–8 °C | 19.2 | 19.2 | n.d. | n.d. |
|   | 37 °C | 17.0 | 21.0 | n.d. | n.d. |
|   | 45 °C | 10.8 | 19.7 | n.d. | n.d. |
| 12 | 2–8 °C | 20.7 | 21.5 | n.d. | n.d. |
|    | 37 °C | 11.8 | 20.1 | n.d. | n.d. |

FIG. 5

| DAY | MATRIX A 2–8 °C | MATRIX B 2–8 °C | MATRIX A AMBIENT | MATRIX B AMBIENT | MATRIX A 37 °C | MATRIX B 37 °C |
|---|---|---|---|---|---|---|
| 0 | 3.56 | 3.35 | 3.56 | 3.35 | 3.56 | 3.35 |
| 1 | 4.00 | 4.20 | n.d. | n.d. | 13.8 | 3.28 |
| 2 | 2.75 | 3.95 | 7.44 | 2.90 | n.d. | n.d. |
| 21 | 12.1 | 3.19 | >20 | 3.48 | >20 | 4.90 |

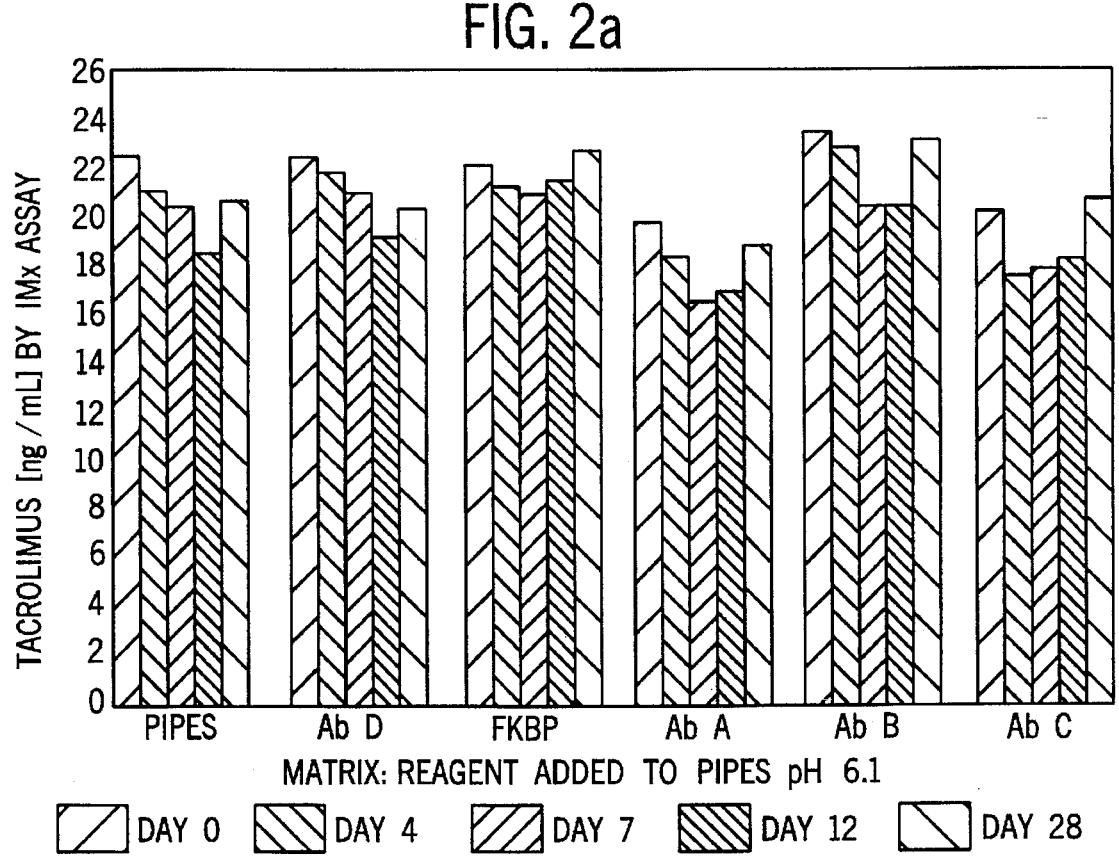

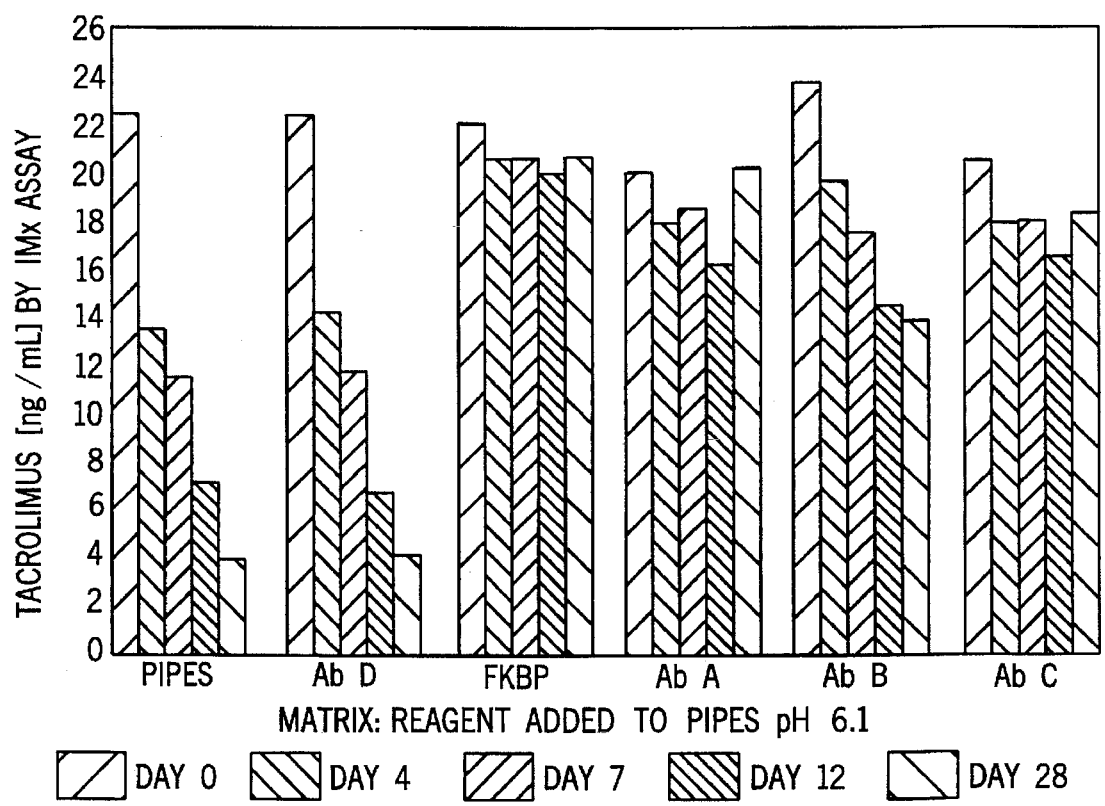

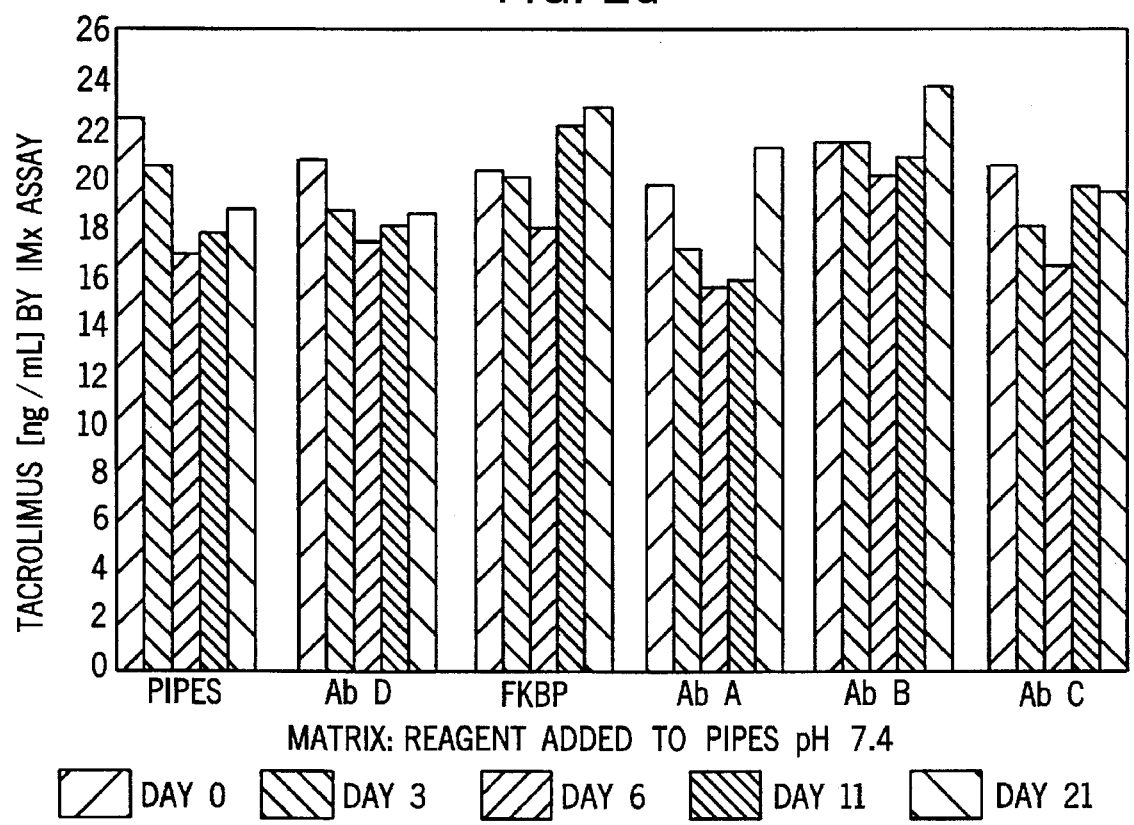

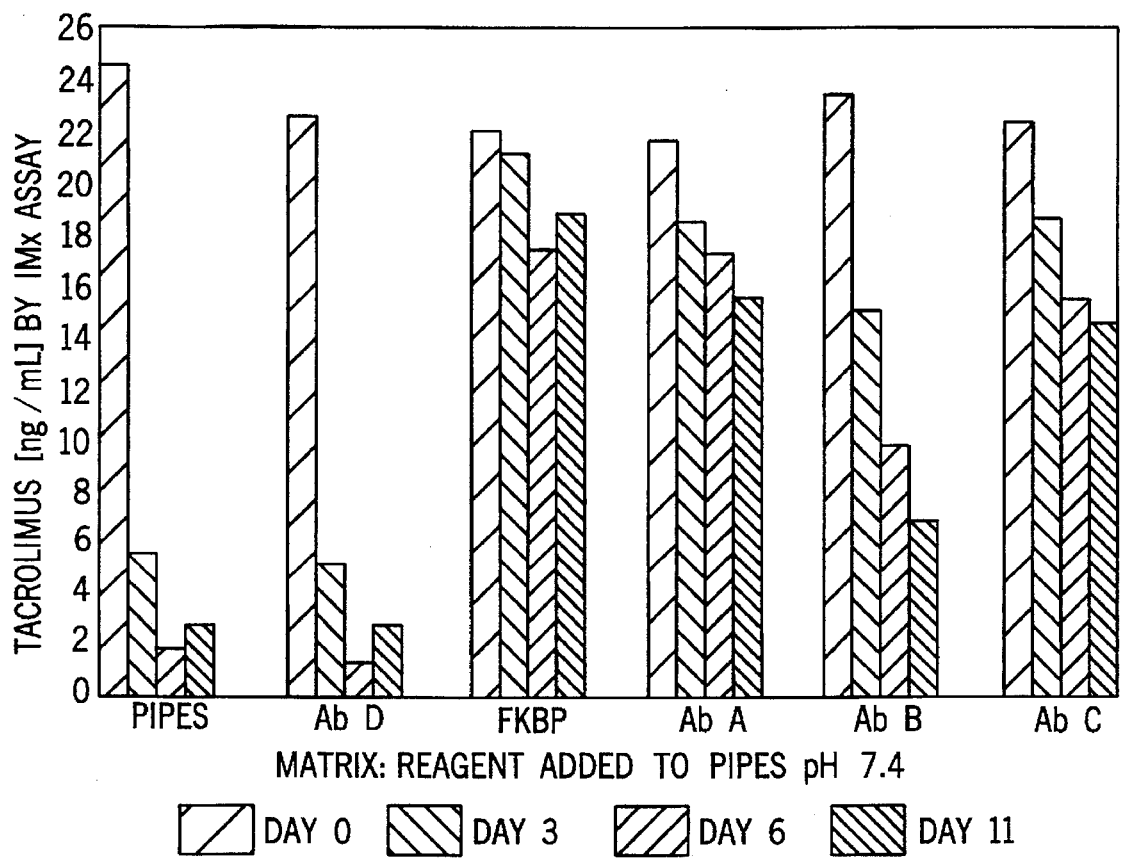

FIG. 3a

UNFORTIFIED

| DAY OF ASSAY / | SAMPLE A | | SAMPLE B | | SAMPLE C | |
|---|---|---|---|---|---|---|
| | 2-8° | 37° | 2-8° | 37° | 2-8° | 37° |
| 0 | 8.67 | 8.29 | 16.1 | 15.6 | 22.0 | 21.6 |
| 4 | 11.3 | 12.7 | 16.0 | 17.7 | 26.4 | >30 |
| 7 | 10.9 | 12.1 | 19.1 | 24.3 | 25.2 | >30 |
| 14 | 10.8 | 20.8 | 18.6 | >30 | 25.3 | >30 |
| 28 | 11.0 | >30 | 17.7 | >30 | 25.9 | >30 |

FIG. 3b

+FKBP 12

| DAY OF ASSAY / | SAMPLE A | | SAMPLE B | | SAMPLE C | |
|---|---|---|---|---|---|---|
| | 2-8° | 37° | 2-8° | 37° | 2-8° | 37° |
| 0 | 8.86 | 9.22 | 16.9 | 15.9 | 23.5 | 21.8 |
| 4 | 7.61 | 9.30 | 14.9 | 15.5 | 24.5 | 22.8 |
| 7 | 11.11 | 13.0 | 15.8 | 17.9 | 23.1 | 24.8 |
| 14 | 8.67 | 10.7 | 14.6 | 15.8 | 24.3 | 24.7 |
| 28 | 9.65 | 10.9 | 17.1 | 18.2 | 25.7 | 27.5 |

FIG. 3c

+ANTI-TACROLIMUS ANTIBODY

| DAY OF ASSAY / | SAMPLE A | | SAMPLE B | | SAMPLE C | |
|---|---|---|---|---|---|---|
| | 2-8° | 37° | 2-8° | 37° | 2-8° | 37° |
| 0 | 10.6 | 11.3 | 20.1 | 17.5 | 29.2 | 25.1 |
| 4 | 11.6 | 12.1 | 19.4 | 19.2 | 26.7 | 26.2 |
| 7 | 11.9 | 11.8 | 17.1 | 16.7 | 22.7 | 21.9 |
| 14 | 12.1 | 11.9 | 18.4 | 18.2 | 27.5 | 26.8 |
| 28 | 11.5 | 11.6 | 18.7 | 19.3 | 26.8 | 28.3 |

FIG. 3d

TACROLIMUS DILUENT

| DAY OF ASSAY / | SAMPLE A | | SAMPLE B | | SAMPLE C | |
|---|---|---|---|---|---|---|
| | 2-8° | 37° | 2-8° | 37° | 2-8° | 37° |
| 0 | 10.9 | 9.59 | 16.0 | 16.1 | 23.8 | 25.1 |
| 4 | 10.4 | 12.4 | 16.7 | 18.6 | 22.2 | 24.9 |
| 7 | 10.1 | 10.4 | 17.0 | 18.7 | 24.7 | 27.6 |
| 14 | 10.4 | 13.2 | 17.1 | 19.8 | 21.5 | 26.7 |
| 28 | 11.7 | 14.7 | 17.7 | 21.6 | 23.5 | 27.6 | ns
STABILIZED STANDARDS AND CALIBRATORS CONTAINING RAPAMYCIN AND TACROLIMUS BOUND TO ANTI-RAPAMYCIN AND ANTI-TACROLIMUS ANTIBODIES

BACKGROUND OF THE INVENTION

1. Technical Field

The present invention is directed to an in vitro aqueous composition comprising a drug, preferably tacrolimus, having enhanced stability. The invention utilizes a binding protein to stabilize the drug in an aqueous matrix.

2. Background

Many drugs which are administered for therapeutic purposes require an accurate and precise analysis of the measurement of the drug in a bodily fluid. Typically, such analytical methods utilize a composition of the drug in one or more calibrators or control solutions. These solutions are used, for example, to create a calibration curve against which the patient sample (having an unknown concentration of the drug of interest) can be accurately extrapolated. In addition, the quality control schemes of most assay systems are predicated on using stable drug standards to assess assay reliability.

As is often the case the drug standard is supplied as one component of an assay kit and thus it is desirable that the kit components are stable to the rigors of transportation, handling and storage. For the ease of use of the technician, it is preferred to provide the assay standards as an essentially aqueous composition. However, many of these same drugs are not stable in aqueous environments and thus tend to degrade rapidly in aqueous matrices. Exemplary among such drugs which are not stable in aqueous environments are the immunosuppressant drugs tacrolimus (also known as FK506) and rapamycin. The development of commercial diagnostic assays are hampered by such unstable compounds. Overcoming these problems represent a challenge in the development of diagnostic assays.

Both tacrolimus and rapamycin have been used as immunosuppressants to control tissue rejection following transplant therapy. Thus, similar to that which is done during cyclosporine therapy, the monitoring of blood concentration of these drugs may be an important aspect of clinical care.

EP 0 293 892 describes an ELISA methodology to measure FK506 (tacrolimus) comprised of 1 ) an ELISA plate coated with anti-FK506 antibodies, 2) an FK506-horseradish peroxidase conjugate which competes with free FK506 and acts as a signal generating reagent and 3) an appropriate substrate for the peroxidase. The protocol requires that the control solution of FK506 used in the assay is made just prior to use from an aliquot of FK506 stored in ethanol at 2°–8° C.

U.S. Pat. No. 5,338,684 to Grenier, et al describes a stabilized composition of FK506 wherein the drug is stored in the presence of whole or lysed blood. The patent discloses that such a composition is stable for at least one day at 37° C. when compared to the drug stored in the absence of whole or lysed blood. The composition is said to useful as a standard or calibrator in assays for FK506. However, such a composition suffers from a drawback in the use of blood or blood components in the composition and the resulting potential biohazard created by handling such products.

Binding proteins for drugs in the immunosuppressant class have been reported. Exemplary among the binding proteins for the drugs tacrolimus or rapamycin are U.S. Pat. Nos. 5,196,352, 5,109,112, International Publication Numbers WO 93/07269 and WO 92/18527, and European Patent Publications 0 584 217 and 0482 189.

International Publication Number WO 92/01052 and European Patent Publication 0 481 673 disclose DNA sequences encoding FK506 binding proteins.

International Publication Number WO 93/25533 discloses a recombinant FKBP fusion protein and it's use in an assay for the purification of tacrolimus.

International Publication Number WO 94/04700 discloses a monoclonal antibody which is specific for an antigenic determinant on both FI<506 and FKBP and an assay employing such an antibody.

International Publication Number WO 95/00174 discloses that antibodies may be stabilized during storage by a solution of a protective ligand having low affinity for the antibody.

Accordingly, a need exists for stable in vitro aqueous compositions of drugs which are unstable under aqueous conditions for utilization as, for example, aqueous standards for diagnostic assays for such drugs.

SUMMARY OF THE INVENTION

The invention provides for a stabilized aqueous matrix comprising a drug normally unstable under aqueous conditions, and an effective amount of a binding protein.

In a preferred matrix of the invention the drug is rapamycin or tacrolimus and the binding protein is FKBP. Most preferred is the binding protein FKBP-12.

Also disclosed is the use of the stabilized matrix of the invention as a standard in a diagnostic assay for the drug.

BRIEF DESCRIPTION OF THE DRAWINGS

FIG. 1 shows the protective effect of FKBP 12 on a solution of tacrolimus.

FIG. 2a shows a stability study of a tacrolimus standard at 2–8 degrees C.

FIG. 2c shows a stability study of a tacrolimus standard at 45 degrees C.

FIG. 2d shows another stability study of a tacrolimus standard at 2–8 degrees C.

FIG. 2f shows another stability study of a tacrolimus standard at 45 degrees C.

FIG. 3 shows the Stabilization of tacrolimus calibrator solutions using FKBP 12, Anti-Tacrolimus Antibody, Tacrolimus Diluent and Unfortified.

FIG. 5 shows the stabilization of rapamycin calibrator solutions in a composition of the invention.

DETAILED DESCRIPTION OF THE INVENTION

Figure 2B:
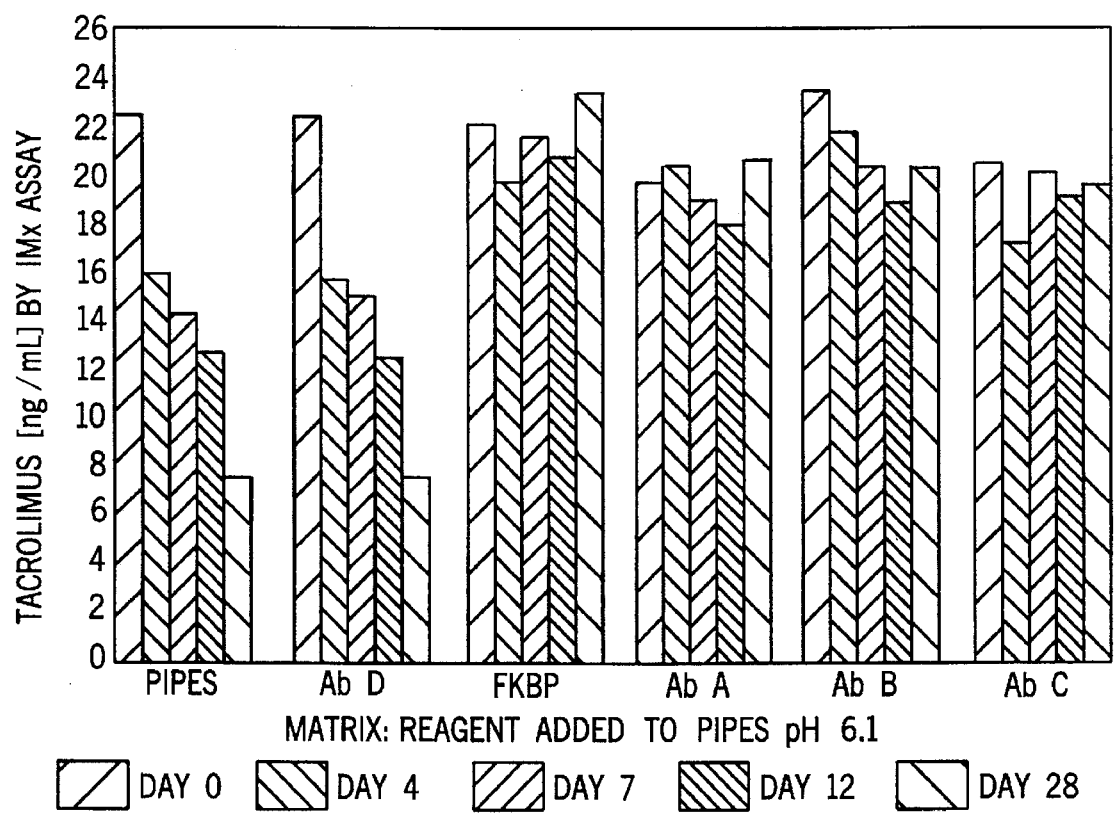
FIG. 2b shows a stability Study of a tacrolimus standard at 37 degrees C.
Figure 2E:
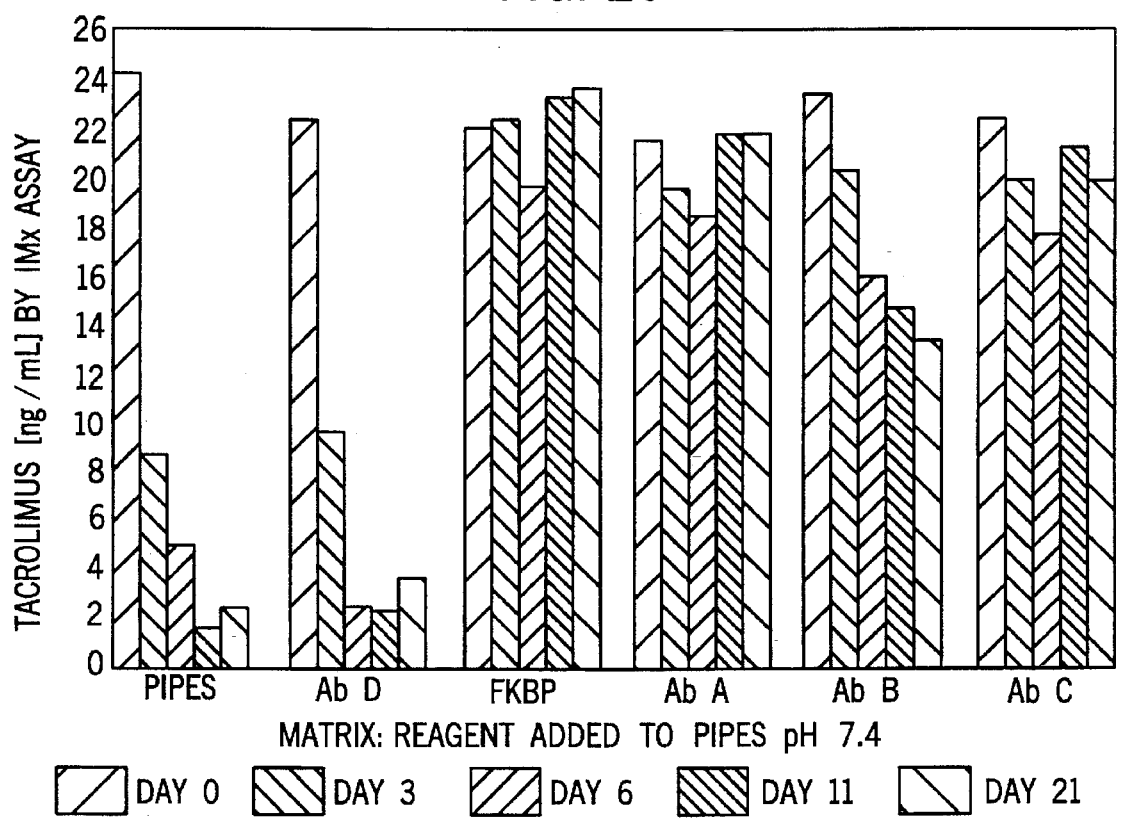
FIG. 2e shows another Stability study of a tacrolimus standard at 37 degrees C.

The terms which follow shall have the following meaning when used throughout this present disclosure:

The term "drug" when used in connection with the stabilized matrix of the invention shall mean a drug or physiologically active agent which would not be stable in an aqueous environment for a period of time, and under conditions suitable for use as, a standard or control in a diagnostic assay for the drug.

"Effective amount" means the amount of binding protein which is effective to stabilize the drug in an aqueous environment under conditions, and for a time, which render the composition suitable for use as a standard in a diagnostic assay.

As stated above, the stabilized matrix of the invention comprises a drug and an amount of a binding protein which is effective to stabilize the drug in an aqueous environment under conditions, and for a time, which render the composition suitable for use as a standard in a diagnostic assay for the drug.

Any drug or physiologically active agent is suitable for use in the invention provided the drug is unstable in an aqueous environment and a suitable binding protein for the drug is available.

Among those drugs which are known to be unstable in aqueous systems are the immunosuppressants compounds rapamycin and tacrolimus. Both rapamycin and tacrolimus are well known in the art to be unstable and, in addition, binding proteins for these compounds have been characterized. Rapamycin and tacrolimus are preferred in the composition of the invention. In addition, other drugs are well known in the art as being subject to degradation when exposed to aqueous solutions, e.g., cyclosporine.

Any of the binding proteins for tacrolimus and rapamycin which are known in the art are suitable for use in the present invention and the binding proteins may be isolated and/or characterized following the methods described above. Furthermore, the techniques for raising antibodies to tacrolimus and/or rapamycin are well known (see, e.g., European Patent Publication 0 293 892 and International Patent Publications WO 94/24304 and WO 94/25022) and no special mention need be made of these methods.

The conditions and the period of time for which the unstable drug should become stabile by utilizing an effective amount of a binding protein will of course be subject to the stability of the drug in an aqueous environment, some drugs being inherently more or less stable than others. In addition, the conditions anticipated for the calibrator or control as well as the parameters of the particular assay should also be considered in determining the period of time for which the composition should remain stable. The compositions of the present invention will be effective to stabilize the drug for at least one day longer than a composition of the drug in the absence of the binding protein as described herein. It is desirable and preferable to maintain stability of the drug over longer periods of time as well as at elevated temperatures. In this respect a preferred compositions of the invention will stabilize the drug for at least 7 days at 37° C. A most preferred composition of the invention will stabilize tacrolimus when stored at pH 6.1 for at least 30 days at 37° C.

While it is has been discovered that the use of a binding protein which specifically binds the unstable drug imparts long term stability to the drug molecule in an aqueous media, it is not known with any certainty the mechanism by which the binding protein and drug interact to attain this result. However, the long-term stability of such compositions has been fully demonstrated as described in more detail below. Furthermore, the structural integrity of tacrolimus after storage in the composition of the invention has been verified by HPLC analysis (data not shown).

The matrix or composition of the inventions is suitable for any use where it is desirable to attain long term stability of the physiologically active moiety contained therein. It is understood, of course, that any intended use must consider the effect of the binding protein on the system where it is used. Preferably, the composition of the invention is useful as a standard in a diagnostic assay for the drug contained therein, i.e., one component of a plurality of reagents which are used to create a calibration curve against which the measurement of a patient sample can be quantified.

EXAMPLE 1

This example illustrates the preparation of an aqueous composition of the invention utilizing FKBP 12. The preparation of FKBP 12 is described in Edalji, et al., J. Prof. Chem. 11:213 (1992). The base matrix is 50 mM piperazine-N,N'-bis[2-ethanesulfonic acid] (PIPES) containing 1% bovine serum albumin, 0.1% TWEEN 20 (Sigma Chemical Co.), and antimicrobials (0.05% (w/v) fluoroquinolone (Abbott Laboratories); 0.05% (w/v) sodium alkyl paraben (NIPASEPT, Nipa Laboratories) and 0.1% (w/v) sodium azide (Sigma)) (hereinafter referred to as P/B/T) at pH 6.1 or 7.4. FKBP 12 is added to P/B/T at a concentration of 1 µg/mL. The matrices are spiked with FK-506 from a stock solution (10 µg/mL stored in methanol at −20° C.) and incubated at 2°–8° C., 37° C., or 45° C. At the times indicated, aliquots of the incubated samples are removed and assayed for the presence of FK-506 using a commercial tacrolimus assay (IMx® Tacrolimus assay, Abbott Laboratories, Abbott Park, Ill. the brochure of which is incorporated herein by reference) following the manufacturer's protocol.

From the results (shown in Table I) it is apparent that the addition of FKBP at 1 µg/mL to the matrix at either pH stabilizes FK-506, preventing any apparent loss of analyte.

EXAMPLE 2

This example illustrates the preparation of an aqueous composition of the invention utilizing tacrolimus monoclonal antibodies. The antibodies are derived from hybridomas prepared from splenocytes of mice immunized with tacrolimus-protein immunogen following published techniques. Three antibodies (designated AbA, AbB, and AbC) are added to P/B/T (pH 6.1 and 7.4) at a concentration of 5 µg/mL and the resulting solutions spiked with tacrolimus to a concentration of 20 ng/mL by dilution from the stock solution described in Example 1. As a control, a monoclonal antibody (AbD) that does not react with tacrolimus is spiked into P/B/T at 5 µg/mL. As an additional comparison, P/B/T is also prepared with 1 µg/mL FKBP and spiked with 20 ng/mL tacrolimus. The solutions containing drug are incubated at 2–8, 37, and 45 degrees Celsius and assayed according to the commercial assay to determine the concentration of tacrolimus remaining after incubation at the time and temperature indicated. The results are shown in FIGS. 2a through 2f. At both pH 6.1 and 7.4 very little deterioration is seen at 2°–8° C. At the elevated temperatures of 37° and 45° C., the decrease in the assayed tacrolimus concentration is dramatic in the unfortified and control (AbD) matrices. The addition of FKBP, AbA, or AbC has a definite stabilizing effect on the drug during incubation at the indicated temperature. It is also noted that not all antibodies are equivalent in this protective capacity, in that AbA and AbC are more effective than AbB in stabilizing tacrolimus. Thus, the accelerated stability study outlined here is also useful in the evaluation of the stabilizing effect, or protective capacity, of antibodies.

EXAMPLE 3

This example illustrates the preparation of an aqueous composition of the invention utilizing tacrolimus monoclonal antibodies and FKBP as additives to prolong the functional life of tacrolimus calibrators. Calibrators having concentrations of tacrolimus of 0, 10, 20, and 30 ng/mL are made up by dilution of a tacrolimus stock solution (Example 1) in P/B/T, pH 6.1. These calibrators are fortified with either 1 µg/mL FKBP or 5 µg/mL anti-tacrolimus antibody. The calibrators are filtered through a 0.2 µm filter. A similar series of calibrators (0, 10, 20, and 30 ng/mL tacrolimus) without FKBP or anti-tacrolimus are prepared in the Tacrolimus assay whole blood diluent (Abbott). All calibrators are stored at 2°–8° or 37° C. until use. A series of tacrolimus samples are prepared in the commercial tacrolimus diluent buffer (Abbott) at 12 (Sample A), 18 (Sample B), and 24 (Sample C) ng/mL and stored until use at −20° C. On the indicated day, a sample of A, B, and C are thawed and the concentration determined in the commercial assay using the fortified calibrators for each of the four diluents. For each set of calibrators at each temperature, a standard curve is generated and the concentration of tacrolimus in the sample computed using point to point data reduction. The results are shown in FIG. 3.

A critical feature determining the functional lifetime of a set of calibrators is that the concentration of the sample determined using the set of calibrators should not change. As shown in FIG. 3, as the tacrolimus in a set of calibrators deteriorates under prolonged storage at 37° C., the apparent concentration of drug in samples determined using that set of calibrators will increase. As can be seen, both the FKBP and anti-tacrolimus antibody fortified calibrator compositions of the invention provide a longer functional lifetime in this accelerated stability study.

EXAMPLE 4

Figure 4A:
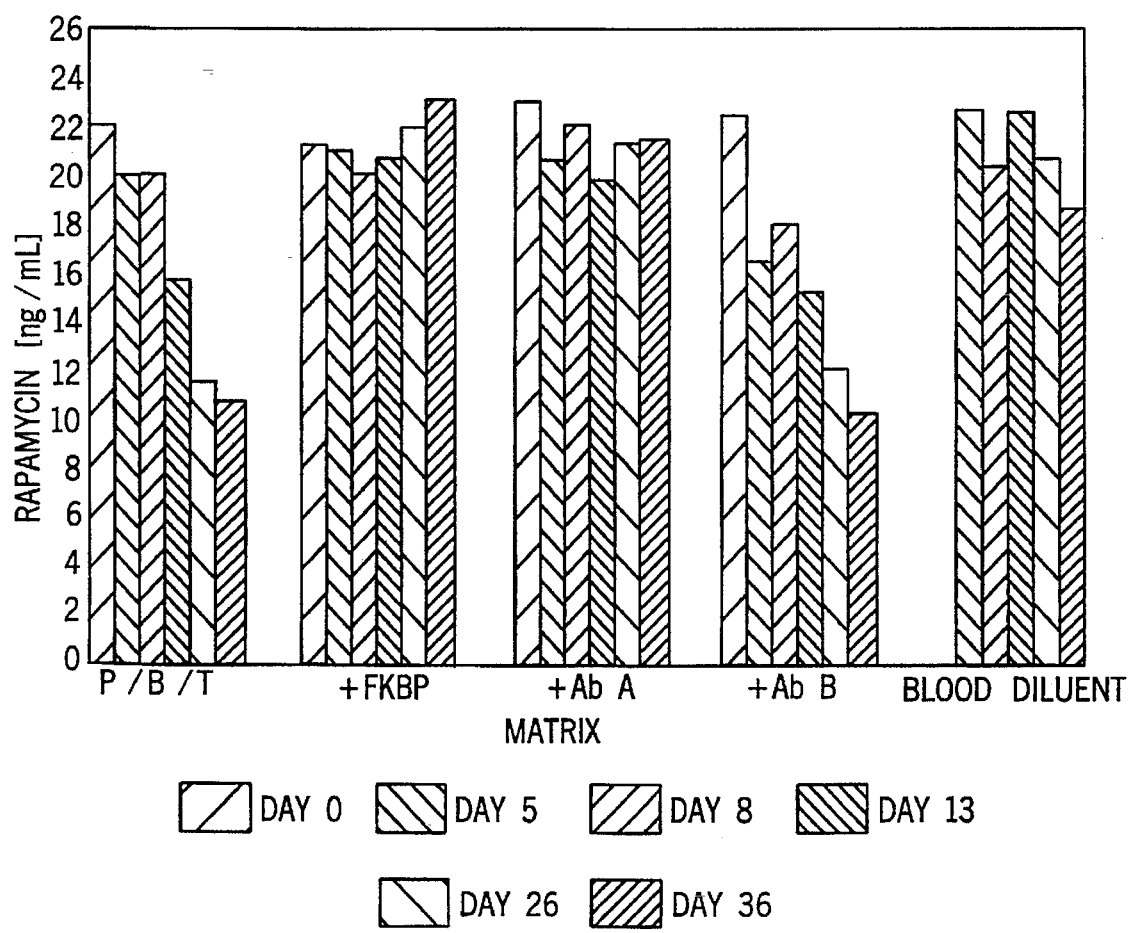
FIG. 4a shows a stability Study of a rapamycin standard at 2–8 degrees C.
Figure 4B:
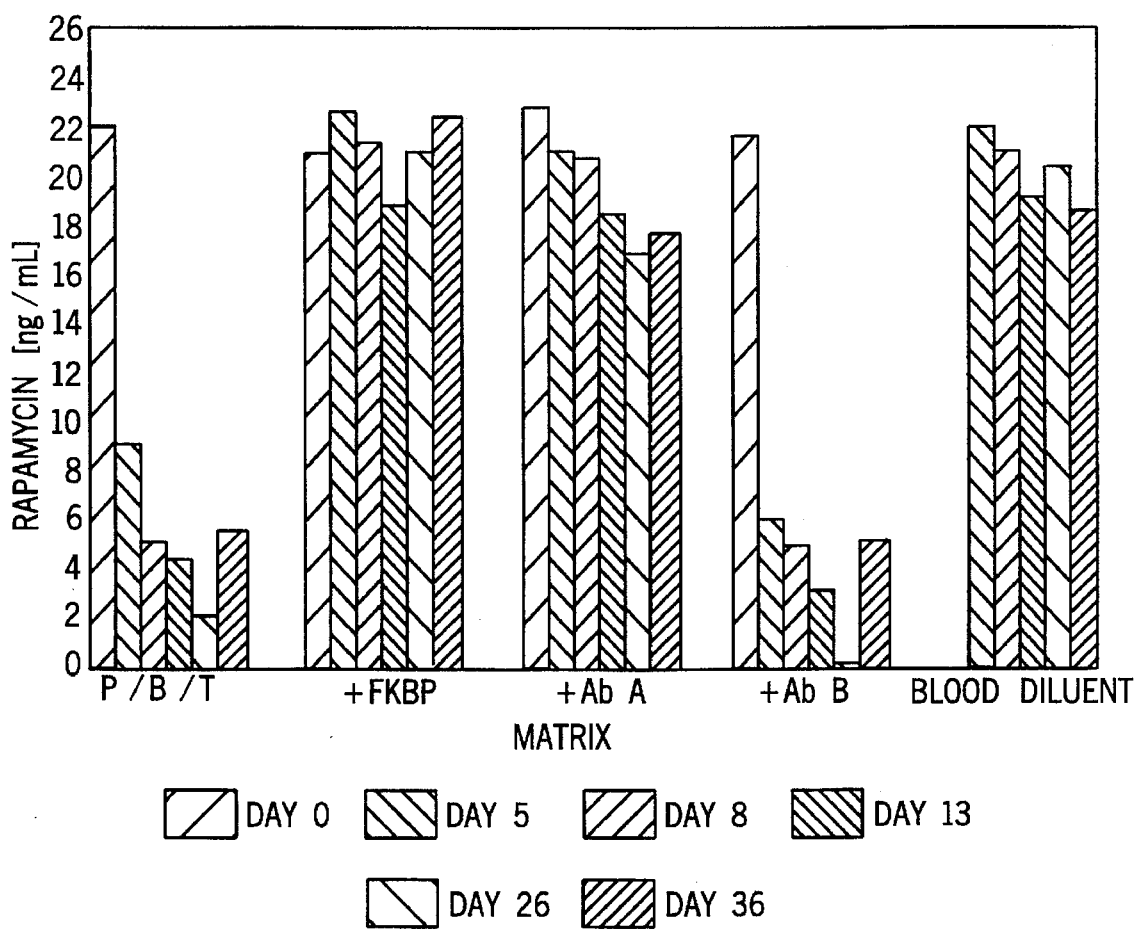
FIG. 4b shows a stability study of a rapamycin standard at ambient temperature.
Figure 4C:
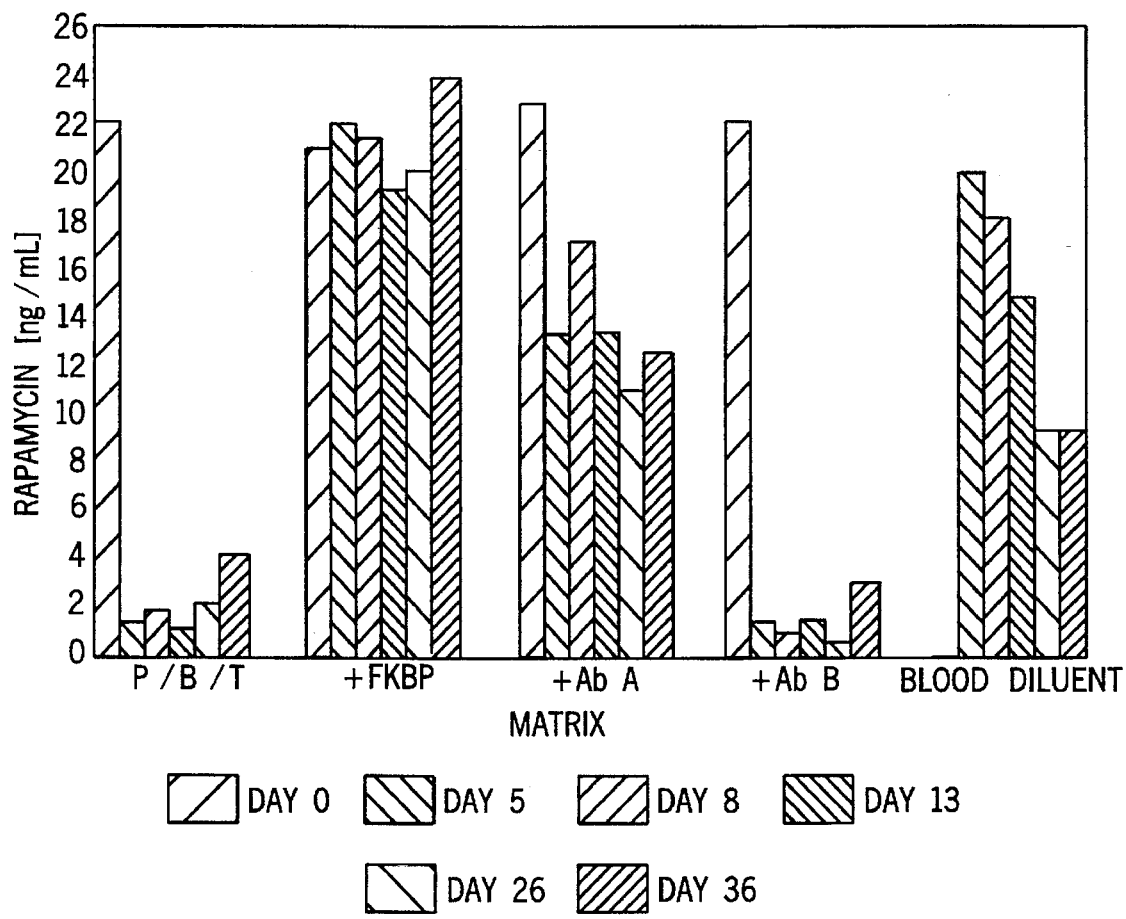
FIG. 4c shows a stability study of a rapamycin standard at 37 degrees C.

This example illustrates the preparation of an aqueous composition of the invention utilizing a binding protein as an additive to prolong the functional life of rapamycin. P/B/T is fortified with FKBP at 3 µg/mL, anti-rapamycin monoclonal antibody at 5 µg/mL (AbA), or a control antibody at 5 µg/mL (AbB). The whole blood calibrator matrix from the commercial assay kit is used for comparison. The matrices are spiked with rapamycin to 40 ng/mL from a stock solution (10 µg/mL in methanol and stored at −20° C.) and stored at 2°–8°, 37° C., and ambient temperature. Calibrators for each days assay are made fresh by dilution from the methanol stock into P/B/T and kept on ice. The assay protocol is similar to that used for the commercial assay, except that the assay microparticles are prepared from an anti-rapamycin monoclonal antibody and the assay conjugate is a rapamycin-CMO-alkaline phosphatase conjugate. The extraction reagent is 1% $ZnSO_4$ in 40% aqueous Methanol. Before assay, sample and calibrators are diluted with an equal volume of whole blood calibrator diluent or P/B/T to give a final concentration of 50% whole blood calibrator diluent and then extracted 1:1 with extraction reagent. The extract is centrifuged and the supernatant is added to the instrument sample well and assayed as previously described. The concentration of samples is read from a standard curve generated using point to point data reduction. The results are shown in FIG. 4a through 4c. The rapid deterioration of rapamycin in P/B/T and P/B/T & control Ab at ambient temperature and 37° C. is evident. The protective effect of either FKBP-12 or the anti-rapamycin antibody is also evident and is similar to that of the tacrolimus whole blood diluent composition. This example also shows the effectiveness of the binding proteins at stabilizing rapamycin at 2°–8° C. at days 26 and 36 of this study.

EXAMPLE 5

The following example demonstrates the preparation of an aqueous composition utilizing the binding protein FKBP-12 to stabilize rapamycin calibrators in an assay. P/B/T at pH 7.4 (matrix A) or P/B/T, pH 7.4 fortified with 1 µg/mL FKBP-12 (matrix B) is used to prepare a calibrator set consisting of 0, 10 and 20 ng/mL rapamycin. A rapamycin control at 4 ng/mL is prepared in the whole blood calibrator diluent and stored at −20° C. The calibrator sets are stored at 2°–8° C., ambient temperature, or 37° C. On the indicated days a control vial is thawed out and assayed as described in Example 4. Concentrations of the control are determined from standard curves obtained from each calibrator set by point to point data reduction.

The results shown in FIG. 5 indicate the deterioration of the rapamycin calibrators at 2°–8° C. within 12 days, at ambient temperature within 2 days and at 37° C. within 1 day. The addition of the FKBP-12 to the calibrator matrix significantly retards calibrator deterioration at all 3 temperatures, thus demonstrating the utility of the binding protein in the aqueous rapamycin calibrator matrix.

We claim:

1. A method for calibrating a sample to be analyzed in an immunoassay to detect the presence or amount of rapamycin in said sample, which comprises:

a) adding to said sample a calibrator composition of rapamycin bound to anti-rapamycin antibodies in amounts sufficient to stabilize rapamycin; and b) extracting said rapamycin from said anti-rapamycin antibodies using an extraction reagent prior to said immunoassay;

c) performing said immunoassay on said calibrator composition; and d) creating a calibration curve based on the results of said immunoassay for use as a standard in an immunoassay for rapamycin in a patient sample.

2. The method of claim 1, wherein said calibrator composition is storage stable at 2–8 degrees C.

3. The method of claim 2, wherein said calibrator composition is storage stable for at least 7 days.

4. The method of claim 3, wherein said calibrator composition is storage stable for at least 30 days.

5. The method of claim 1, wherein said calibrator composition is storage stable at ambient temperature.

6. The method of claim 5, wherein said calibrator composition is storage stable for at least 7 days.

7. The method of claim 6, wherein said calibrator composition is storage stable for at least 30 days.

8. The method of claim 1, wherein said calibrator composition is storage stable at 37 degrees C.

9. The method of claim 8, wherein said calibrator composition is storage stable for at least 7 days.

10. The method of claim 9, wherein said calibrator composition is storage stable for at least 30 days.

11. The method of claim 1, further comprising the step of diluting said sample and said calibrator composition prior to said extraction with said extraction reagent.

12. A method for stabilizing an aqueous composition containing a drug normally unstable under aqueous conditions, which comprises adding an effective amount of a binding protein thereto, wherein said drug is rapamycin and said binding protein is anti-rapamycin antibodies.

13. The method of claim 12, wherein said aqueous composition is storage stable at 2-8 degrees C.

14. The method of claim 13, wherein said aqueous composition is storage stable for at least 7 days.

15. The method of claim 14, wherein said aqueous composition is storage stable for at least 30 days.

16. The method of claim 12, wherein said aqueous composition is storage stable at ambient temperature.

17. The method of claim 16, wherein said aqueous composition is storage stable for at least 7 days.

18. The method of claim 17, wherein said aqueous composition is storage stable for at least 30 days.

19. The method of claim 12, wherein said aqueous composition is storage stable at 37 degrees C.

20. The method of claim 19, wherein said aqueous composition is storage stable for at least 7 days.

21. The method of claim 20, wherein said aqueous composition is storage stable for at least 30 days.

22. A method for calibrating a sample to be analyzed in an immunoassay to detect the presence or amount of tacrolimus in said sample, which comprises:

a) adding to said sample a calibrator composition of tacrolimus bound to anti-tacrolimus antibodies in amounts sufficient to stabilize tacrolimus; and b) extracting said tacrolimus from said anti-tacrolimus antibodies using an extraction reagent prior to said immunoassay;

c) performing said immunoassay on said calibrator composition; and d) creating a calibration curve based on the results of said immunoassay for use as a standard in an immunoassay for tacrolimus in a patient sample.

23. The method of claim 22, wherein said aqueous composition is storage stable at 2-8 degrees C.

24. The method of claim 23, wherein said aqueous composition is storage stable for at least 7 days.

25. The method of claim 24, wherein said aqueous composition is storage stable for at least 30 days.

26. The method of claim 22, wherein said aqueous composition is storage stable at ambient temperature.

27. The method of claim 26, wherein said aqueous composition is storage stable for at least 7 days.

28. The method of claim 27, wherein said aqueous composition is storage stable for at least 30 days.

29. The method of claim 22, wherein said aqueous composition is storage stable at 37 degrees C.

30. The method of claim 29, wherein said aqueous composition is storage stable for at least 7 days.

31. The method of claim 30, wherein said aqueous composition is storage stable for at least 30 days.

32. The method of claim 22, further comprising the step of diluting said sample and said aqueous composition prior to said extraction with said extraction reagent.

33. A method for stabilizing an aqueous composition containing a drug normally unstable under aqueous conditions, which comprises adding an effective amount of a binding protein thereto, wherein said drug is tacrolimus and said binding protein is anti-tacrolimus antibodies.

34. The method of claim 33, wherein said aqueous composition is storage stable at 2-8 degrees C.

35. The method of claim 34, wherein said aqueous composition is storage stable for at least 7 days.

36. The method of claim 35, wherein said aqueous composition is storage stable for at least 30 days.

37. The method of claim 33, wherein said aqueous composition is storage stable at ambient temperature.

38. The method of claim 37, wherein said aqueous composition is storage stable for at least 7 days.

39. The method of claim 38, wherein said aqueous composition is storage stable for at least 30 days.

40. The method of claim 33, wherein said aqueous composition is storage stable at 37 degrees C.

41. The method of claim 40, wherein said aqueous composition is storage stable for at least 7 days.

42. The method of claim 41, wherein said aqueous composition is storage stable for at least 30 days.

* * * * *

UNITED STATES PATENT AND TRADEMARK OFFICE
CERTIFICATE OF CORRECTION

PATENT NO. : 5,635,406
DATED : June 3, 1997
INVENTOR(S) : Grenier et al.

It is certified that error appears in the above-indentified patent and that said Letters Patent is hereby corrected as shown below:

Column 7, line 34, change "aqueous" to --calibrator--.

Column 7, line 36, change "aqueous" to --calibrator--.

Column 7, line 38, change "aqueous" to --calibrator--.

Column 8, line 1, change "aqueous" to --calibrator--.

Column 8, line 3, change "aqueous" to --calibrator--.

Column 8, line 5, change "aqueous" to --calibrator--.

Column 8, line 7, change "aqueous" to --calibrator--.

Column 8, line 9, change "aqueous" to --calibrator--.

Column 8, line 11, change "aqueous" to --calibrator--.

Column 8, line 14, change "aqueous" to --calibrator--.

Signed and Sealed this

Twenty-eighth Day of October, 1997

Attest:

BRUCE LEHMAN

Attesting Officer

Commissioner of Patents and Trademarks